(12) United States Patent
Kasuya et al.

(10) Patent No.: US 8,038,958 B2
(45) Date of Patent: Oct. 18, 2011

(54) METHOD FOR DECOMPOSING AND RECOVERING ISOCYANATE COMPOUND

(75) Inventors: Fumihiko Kasuya, Hyogo (JP); Masahiro Yamagata, Hyogo (JP); Shigetoshi Suzuki, Ibaraki (JP); Tadashi Yoshida, Ibaraki (JP)

(73) Assignees: Kobe Steel, Ltd., Kobe-shi (JP); Mitsui Chemicals, Inc., Tokyo (JP)

( * ) Notice: Subject to any disclaimer, the term of this patent is extended or adjusted under 35 U.S.C. 154(b) by 731 days.

(21) Appl. No.: 11/995,397

(22) PCT Filed: Jul. 12, 2006

(86) PCT No.: PCT/JP2006/313870
§ 371 (c)(1),
(2), (4) Date: Jan. 11, 2008

(87) PCT Pub. No.: WO2007/007791
PCT Pub. Date: Jan. 18, 2007

(65) Prior Publication Data
US 2009/0275776 A1    Nov. 5, 2009

(30) Foreign Application Priority Data

Jul. 12, 2005    (JP) .................................. 2005-202419

(51) Int. Cl.
*B01J 3/00*    (2006.01)
*B01J 19/00*    (2006.01)

(52) U.S. Cl. ...................... 422/184.1; 422/226; 422/228; 422/229; 422/242

(58) Field of Classification Search .............. 422/184.1, 422/226, 228, 229, 242
See application file for complete search history.

(56) References Cited

U.S. PATENT DOCUMENTS
2,625,887 A * 1/1953 Anderson ........................ 91/503
(Continued)

FOREIGN PATENT DOCUMENTS
EP    0 492 556 A1    7/1992
(Continued)

OTHER PUBLICATIONS

Extended European Search Report issued Aug. 11, 2010, in Patent Application No. 06768134.6-2103 / 1903026 PCT/JP2006313870.

(Continued)

*Primary Examiner* — Jennifer A Leung

(74) *Attorney, Agent, or Firm* — Oblon, Spivak, McClelland, Maier & Neustadt, L.L.P.

(57) ABSTRACT

The present invention relates to a method for decomposing and recovering an isocyanate compound, which comprises: continuously mixing and dispersing into water at high pressure and high temperature an isocyanate compound having at least one isocyanate group or group derived from an isocyanate group in a molten state or solution state, supplying a liquid mixture containing the isocyanate compound and the water at high pressure and high temperature continuously to a reactor, followed by subjecting the isocyanate compound to a decomposition reaction in the reactor, and recovering a raw material for the isocyanate compound or a derivative thereof; and an apparatus for decomposing and recovering an isocyanate compound, which comprises: a reactor which brings water at high pressure and high temperature into contact with an isocyanate compound having at least one isocyanate group or group derived from an isocyanate group to cause a decomposition reaction, a water supply line which continuously supplies the water at high pressure and high temperature to a reactor, a compound supply line which continuously supplies the isocyanate compound in a molten state or solution state to the water supply line, an on-off valve which communicates the compound supply line with a vicinity of a communication portion of the water supply line to the reactor, a dehydrating device which conducts a dehydration of a decomposition reaction product discharged from the reactor, and a purification device which purifies the decomposition reaction product after the dehydration.

4 Claims, 4 Drawing Sheets

U.S. PATENT DOCUMENTS

| | | | |
|---|---|---|---|
| 3,225,084 A | 12/1965 | Koch | |
| 4,137,266 A | 1/1979 | Cassata | |
| 4,281,935 A * | 8/1981 | Cramer et al. | 366/182.1 |
| 5,210,284 A | 5/1993 | Mizia et al. | |
| 6,054,103 A * | 4/2000 | Mandel | 422/208 |
| 6,255,529 B1 | 7/2001 | Nagase et al. | |
| 6,462,230 B1 | 10/2002 | Nagase et al. | |
| 6,630,517 B2 | 10/2003 | Nishida et al. | |
| 6,660,236 B1 * | 12/2003 | Kodama et al. | 422/188 |

FOREIGN PATENT DOCUMENTS

| | | |
|---|---|---|
| EP | 0 854 165 A1 | 7/1998 |
| EP | 0 976 719 A1 | 2/2000 |
| EP | 1 006 143 A1 | 6/2000 |
| GB | 991387 | 5/1965 |
| GB | 1047101 | 11/1966 |
| JP | 3-500264 | 1/1991 |
| JP | 3-16328 | 3/1991 |
| JP | 4-275269 | 9/1992 |
| JP | 5-31000 | 2/1993 |
| JP | 5-271328 | 10/1993 |
| JP | 9-151270 | 6/1997 |
| JP | 10-279539 | 10/1998 |
| JP | 2002-173471 | 6/2002 |
| KR | 2000-70737 | 11/2000 |
| TW | 340124 | 9/1998 |
| TW | 358106 | 5/1999 |

OTHER PUBLICATIONS

Jane-Jane Ou, et al., "Mixing of Chemically Reactive Fluids by Swirling in a Tubular Reactor", Chemical Engineering Science, vol. 38, No. 8, XP-002589648, 1983, pp. 1323-1329.

Taiwanese Office Action issued Sep. 10, 2010, in Patent Application No. 095125501 (with English-language translation).

* cited by examiner

US 8,038,958 B2

METHOD FOR DECOMPOSING AND RECOVERING ISOCYANATE COMPOUND

TECHNICAL FIELD

The present invention relates to a method for decomposing and recovering an isocyanate compound, including bringing an isocyanate compound obtained, for example, as distillation residues which are discarded in a chemical plant into contact with water at high pressure and high temperature to conduct a decomposition treatment, followed by recovering the isocyanate compound as a raw material therefor or a derivative thereof thereby enabling re-utilization thereof; and an apparatus for decomposing and recovering the same.

BACKGROUND ART

In the case of synthesizing various chemical products industrially in chemical plants, it has been known that by-products other than the aimed products are formed or unreacted products are remained. For example, in a polymerizing reaction plant, an apparatus for separating a resultant polymer and an unreacted monomer in a reaction vessel is essentially provided and the recovered unreacted monomer is usually utilized again as a raw material for the polymerizing reaction. In the polymerizing reaction, while it has also been known that multimers such as oligomers are by-produced, in the case where the multimer remains in the polymer, since this results in a drawback that chemical products having aimed properties cannot be obtained, or the properties of the chemical products are degraded with time, a separating and removing step for the multimer is often provided. While the unreacted monomer can be made re-utilizable by merely incorporating it into a raw material supply line, the multimer cannot be handled in the same manner as the monomer, and therefore, it is subjected exclusively to incinerating treatment or discarding treatment.

Furthermore, not only in the polymerizing reaction plants but also in chemical plants for synthesizing low molecular compounds, by-products or multimers such as dimers or trimers of the aimed compounds are formed and it is thus necessary to separate by-products and multimers from the aimed compounds, for example, by a distillation. In the case of the low molecular compounds, although separation of by-products is relatively easy, since it is often difficult to separate the multimer and the aimed compound, the multimer and the aimed product are often contained in the wastes such as distillation residues. There are scarce methods of effectively utilizing these wastes and, since only the incineration or discarding treatment is applied, this has resulted a problem in view of the resource saving.

On the other hand, it has been attempted in recent years to detoxify wastes or obtain effectively utilizable products by using hydrolysis or oxidizing reaction in water at high pressure and high temperature. For example, it has been proposed a method of detoxifying liquid wastes by utilizing an oxidizing reaction in a supercritical or subcritical state (for example, refer to Patent Document 1), a method of hydrolyzing various high molecular compounds by using water in a supercritical or subcritical state (for example, refer to Patent Document 2) and, further, a method of obtaining pure terephthalic acid and glycol from polyethylene terephthalate wastes (for example, refer to Patent Documents 3 or 4).

However, while the method proposed in Patent Document 1 is important as the detoxifying method, since it accompanies the oxidizing reaction, this results in a problem for the usefulness of the obtained materials. Further, there is no description in any other patent documents about a method of efficiently decomposing and recovering compounds containing oligomers or dimers or higher multimers, or a decomposing and recovering apparatus.

On the other hand, while methods of decomposing isocyanate compounds and recovering them as amine compounds (for example, refer to Patent Documents 5, 6, 7 or 8) have been disclosed, since each of them is a batchwise method, enormous energy for cooling or heating as well as depressurization or pressurization upon replacement of batch is required and the processing amount is also limited in view of the scale of the apparatus, and therefore, it cannot be said that they are industrially suitable.

Then, it has been proposed a method for continuously decomposing and recovering an isocyanate compound and an apparatus for decomposing and recovering them, in which multimers or other by-products of isocyanate compounds by-produced in production lines of isocyanate compounds as target compounds to be hydrolyzed is selected among the wastes in the chemical plants for which no other treating methods than incineration or discarding are present, and the isocyanate compounds are decomposed and recovered as a raw material or a derivative thereof as intermediate material thereby enabling the effective re-utilization thereof (hereinafter referred to also as a conventional example).

In the followings, the conventional example is described with reference to the appended drawings. FIG. 4 is a schematic explanatory view showing an example of an apparatus for decomposing and recovering an isocyanate compound, which is for practicing a method for decomposing and recovering the same according to the conventional example. The apparatus for decomposing and recovering the isocyanate compound includes a longitudinal cylindrical reactor 51 that brings water at high pressure and high temperature into contact with an isocyanate compound thereby causing decomposition reaction. A water supply line 52 intervened with a supply pump 52a for pressurizing water and a heater 52b for heating the water at high pressure pressurized by the supply pump 52a is in communication to the bottom of the reactor 51. Furthermore, a compound supply line 53 intervened with a supply pump 53a for pressurizing the isocyanate compound in a molten state or liquid state, and a heater 53b for heating the isocyanate compound in a molten state or liquid state pressurized by the supply pump 53a is in communication with lateral side near the lower portion of the reactor 51.

Moreover, a decomposition reaction product discharge line 54 for supplying a decomposition reaction product formed by decomposition at a temperature of the reactor 51 of from 190 to 300° C. is in communication with a dehydrating column 55 as a dehydrating device from the decomposition reaction product discharge port at the top of the reactor 51. Further, a decomposition reaction product supply line 56 for supplying a decomposition reaction product which is dehydrated as well as removed with $CO_2$ in the dehydrating column 55 is in communication with a depressurized distillation column 57 as a purifying apparatus from the top of the dehydrating column 55. Then, it is adapted such that the decomposition reaction product which is dehydrated as well as removed with $CO_2$ by distillation in the depressurized distillation column 57 is separated into aimed decomposed and recovered product (raw material for the isocyanate compound or derivatives thereof) and undecomposed products (undecomposed compounds).

According to the apparatus for decomposing and recovering the isocyanate compound of the conventional example, an isocyanate compound having at least one isocyanate group or a group derived from an isocyanate group is brought into contact with water at high pressure and high temperature water to thereby decompose the same, whereby the raw material for the isocyanate compound or the derivative thereof can be recovered. Further, since the decomposition reaction can be conducted effectively by setting the weight of the water at high pressure and high temperature to 0.5 to 5.0 times the weight of the isocyanate compound in the reactor 51 and supplying the isocyanate compound in a molten state at 120 to 180° C. or in a solution state in which the isocyanate compound is dissolved in the solvent, the recovery rate of the raw material for the isocyanate compound or the derivative thereof is improved (for example, refer to Patent Documents 9 or 10).

Patent Document 1: JP-T-3-500264
Patent Document 2: JP-A-5-031000
Patent Document 3: JP-B-3-016328
Patent Document 4: JP-A-5-271328
Patent Document 5: GB Patent No. 0,991,387
Patent Document 6: GB Patent No. 1,047,101
Patent Document 7: U.S. Pat. No. 3,225,084
Patent Document 8: U.S. Pat. No. 4,137,266
Patent Document 9: JP-A-10-279539
Patent Document 10: U.S. Pat. No. 6,630,517

DISCLOSURE OF THE INVENTION

Problem that the Invention is to Solve

According to the method for decomposing and recovering the isocyanate compound and the apparatus for decomposing and recovering the same of the conventional examples described in JP-A-10-279539 and U.S. Pat. No. 6,630,517, isocyanate compounds that have been obliged to be incinerated or discarded can be continuously decomposed and the raw material for the isocyanate compound or the derivative thereof can be recovered. However, since it is difficult to rapidly disperse the isocyanate compounds in the water at high pressure and high temperature and the isocyanate compound is sometimes polymerized, they cannot be always considered satisfactory from a standpoint of the recovery efficiency for the raw material for the isocyanate compound or the derivative thereof and further improvement has been desired for the recovery efficiency. By the way, for rapidly dispersing the isocyanate compound in the water at high pressure and high temperature, it is necessary to increase the linear velocity of the water at high pressure and high temperature. For this purpose, the reactor may be elongated. However, since this cannot be attained substantially, means for elongating the reactor cannot be adopted.

Accordingly, it is an object of the invention to provide a method for decomposing and recovering an isocyanate compound and an apparatus for decomposing and recovering the same that enable improvement in the recovery efficiency of the raw material for the isocyanate compound or the derivative thereof by rapidly dispersing the isocyanate compound in water at high pressure and high temperature without elongating the reactor.

Means for Solving the Problem

As a result of intensive studies, the present inventors have found that, by introducing an isocyanate compound to a water supply line while increasing the linear velocity of water at high pressure and high temperature flowing in the water supply line, the isocyanate compound can be dispersed rapidly in the water at high pressure and high temperature. Further, the present inventors have achieved the invention by solving the problem of clogging at the introduction portion of an isocyanate compound to the water supply line (compound supply port open to the water supply line) due to the polymerization of the isocyanate compound.

That is, the present invention relates to the following (1) to (10).

(1) A method for decomposing and recovering an isocyanate compound, which comprises:

continuously mixing and dispersing into water at high pressure and high temperature an isocyanate compound having at least one isocyanate group or group derived from an isocyanate group in a molten state or solution state;

supplying a liquid mixture containing the isocyanate compound and the water at high pressure and high temperature continuously to a reactor, followed by subjecting the isocyanate compound to a decomposition reaction in the reactor; and recovering a raw material for the isocyanate compound or a derivative thereof (2) The method for decomposing and recovering an isocyanate compound according to (1) above, wherein the water at high pressure and high temperature has a linear velocity of 0.5 m/s or higher at the position for mixing the isocyanate compound in a molten state or solution state.

(3) The method for decomposing and recovering an isocyanate compound according to (1) or (2) above, wherein the liquid mixture containing the isocyanate compound and the water at high pressure and high temperature is ascended as a swirling flow in the reactor.

(4) An apparatus for decomposing and recovering an isocyanate compound, which comprises:

a reactor which brings water at high pressure and high temperature into contact with an isocyanate compound having at least one isocyanate group or group derived from an isocyanate group to cause a decomposition reaction;

a water supply line which continuously supplies the water at high pressure and high temperature to a reactor;

a compound supply line which continuously supplies the isocyanate compound in a molten state or solution state to the water supply line;

an on-off valve which communicates the compound supply line with a vicinity of a communication portion of the water supply line to the reactor;

a dehydrating device which conducts a dehydration of a decomposition reaction product discharged from the reactor; and a purification device which purifies the decomposition reaction product after the dehydration.

(5) The apparatus for decomposing and recovering an isocyanate compound according to (4) above, wherein the on-off valve includes:

a water flow tubular member intervened in the water supply line, the water flow tubular member having a water flow channel through which the water at high pressure and high temperature flows, a compound supply port opened into the water flow channel, wherein the isocyanate compound in a molten state or solution state supplied from the compound supply line flows out from the compound supply port, and a retractable valve rod which inhibits an inflow of the water at high pressure and high temperature into the compound supply port in a closed state in which an outflow of the isocyanate compound into the water flow channel is shut off.

(6) The apparatus for decomposing and recovering an isocyanate compound as a decomposition target according to (4) above, wherein the reactor includes:

a vertical cylindrical vessel body having a discharge port for the decomposition reaction product at the top thereof and a liquid mixture supply port in communication with the water supply line at the bottom thereof, and a liquid swirling device disposed in the vessel body, which ascends a liquid mixture entering from the liquid mixture supply port as a swirling flow.

(7) The apparatus for decomposing and recovering an isocyanate compound as a decomposition target according to (5), wherein the reactor includes:

a vertical cylindrical vessel body having a discharge port for the decomposition reaction product at the top thereof and a liquid mixture supply port in communication with the water supply line at the bottom thereof, and a liquid swirling device disposed in the vessel body, which ascends a liquid mixture entering from the liquid mixture supply port as a swirling flow.

(8) The apparatus for decomposing and recovering an isocyanate compound as a decomposition target according to (6), wherein the liquid swirling device includes:

a blade support member disposed at the radial center of the vessel body, and a spiral blade fixed spirally to the blade support member, the spiral blade having an outer circumferential end which contacts with the inner peripheral surface of the vessel body.

(9) The apparatus for decomposing and recovering an isocyanate compound as a decomposition target according to (7), wherein the liquid swirling device includes:

a blade support member disposed at the radial center of the vessel body, and a spiral blade fixed spirally to the blade support member, the spiral blade having an outer circumferential end which contacts with the inner peripheral surface of the vessel body.

(10) The apparatus for decomposing and recovering an isocyanate compound as a decomposition target according to any one of (4) to (9) above, wherein the water at high pressure and high temperature and the isocyanate compound in a molten state or solution state are respectively supplied under pressure with a multi piston pump.

Advantage of the Invention

According to the method for decomposing and recovering the isocyanate compound according to any one of (1) to (3) above or the apparatus for decomposing and recovering the isocyanate compound according to any one of (4) to (10) above, since the isocyanate compound in a molten state or solution state is continuously mixed into the water at high pressure and high temperature at high linear velocity, the isocyanate compound can be dispersed rapidly in the water at high pressure and high temperature without any requirement for elongating the reactor. Then, since the isocyanate compound in the liquid mixture containing the isocyanate compound and the water at high pressure and high temperature supplied continuously to the reactor is subjected to decomposition reaction at a high efficiency in the reactor, the recovery efficiency of the raw material for the isocyanate compound or the derivative thereof is increased. Further, setting of the linear velocity of the water at high pressure and high temperature to 0.5 m/s or higher is a preferred embodiment for rapidly dispersing the isocyanate compound into the water at high pressure and high temperature.

According to the method for decomposing and recovering the isocyanate compound according to (3) above or the apparatus for decomposing and recovering the isocyanate compound according (6) or (7) above, the liquid mixture containing the isocyanate compound and the water at high pressure and high temperature flowing into the reactor ascends as a swirling flow. Accordingly, since $CO_2$ evolved by the decomposition reaction of the isocyanate compound accompanies the swirling flow as bubbles, $CO_2$ does not blow out upwardly above the reactor. Consequently, since the decomposition reaction product is supplied from the reactor to the dehydrating device without any trouble, this can contribute to the improvement of the recovery efficiency of the raw material for the isocyanate compound or the derivative thereof.

According to the apparatus for decomposing and recovering the isocyanate compound according to (5) above, since the on-off valve has a retractable valve rod which inhibits the inflow of the water at high pressure and high temperature into the compound supply port in a closed state in which the outflow of the isocyanate compound into the water flow channel is shut off, the water at high pressure and high temperature does not stay at the compound supply port in the closed state and, at the same time with the opening of the valve, the isocyanate compound intrudes into the water at high pressure and high temperature flowing at a high linear velocity. Accordingly, since polymerization of the isocyanate compound due to the staying of the water at high pressure and high temperature at the compound supply port does not occur and the compound supply port is not clogged, the isocyanate compound can be mixed into the water at high pressure and high temperature without any trouble.

According to the apparatus for decomposing and recovering the isocyanate compound according to (10) above, since a supply pump which supplies under pressure the water at high pressure and high temperature and another supply pump which supplies under pressure the isocyanate compound in a molten state or solution state each are a multi-piston pump, pulsation during supply of the water at high pressure and high temperature and the isocyanate compound can be decreased. Accordingly, since a large amount of the water at high pressure and high temperature and the isocyanate compound can be supplied in comparison with the case where the pulsation is large, this can contribute to the improvement for the recovery efficiency of the raw material for the isocyanate compound or the derivative thereof.

| Description of Numerals and Signs | |
|---|---|
| 1 | reactor |
| 11 | vessel body |
| 11a | discharge port |
| 11b | liquid mixture supply port |

-continued

Description of Numerals and Signs

| | |
|---|---|
| 12 | liquid swirling device |
| 12a | blade support member |
| 12b | spiral blade |
| 2 | water supply line |
| 2a | supply pump |
| 2b | heater |
| 3 | compound supply line |
| 3a | supply pump |
| 3b | heater |
| 4 | decomposition reaction product discharge line |
| 5 | dehydrating column |
| 6 | decomposition reaction product supply line |
| 7 | depressurized distillation column |
| 8 | on-off valve |
| 8a | water flow tubular member |
| 8b | water flow channel |
| 8c | compound supply port |
| 8d | valve rod |
| 8e | valve box |
| 8f | air cylinder |
| 8g | piston |
| 8h | coil spring |
| 8i | valve rod stroke control rod |

BEST MODE FOR CARRYING OUT THE INVENTION

In the followings, an apparatus for decomposing and recovering an isocyanate compound according to an embodiment of the invention for practicing a method for decomposing and recovering the isocyanate compound according to the invention is described with reference to the appended drawings.

Figure 1:
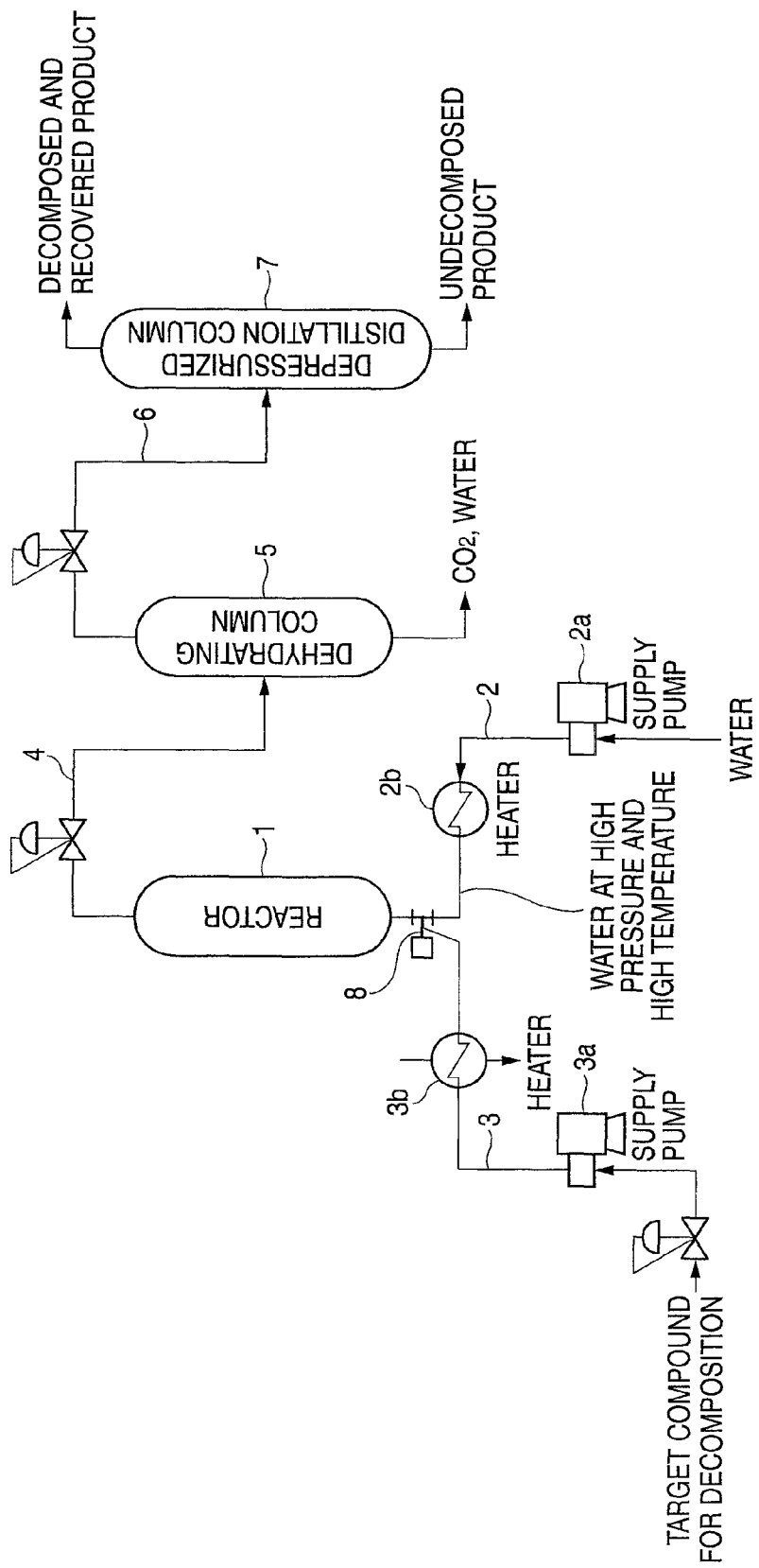
FIG. 1 is a schematic explanatory view showing an example of an apparatus for decomposing and recovering an isocyanate compound according to an embodiment of the invention.
Figure 2:
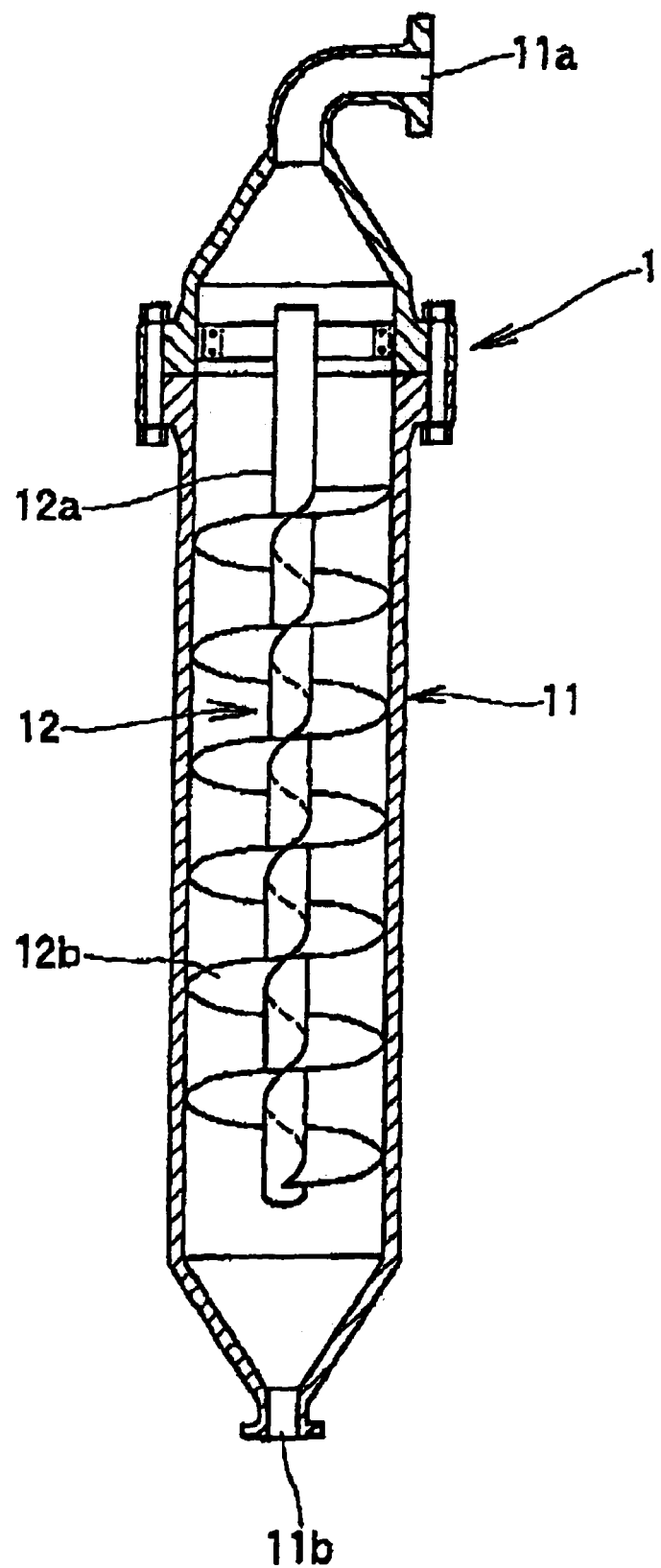
FIG. 2 is a cross sectional view of a reactor of an apparatus for decomposing and recovering an isocyanate compound according to an embodiment of the invention.
Figure 3:
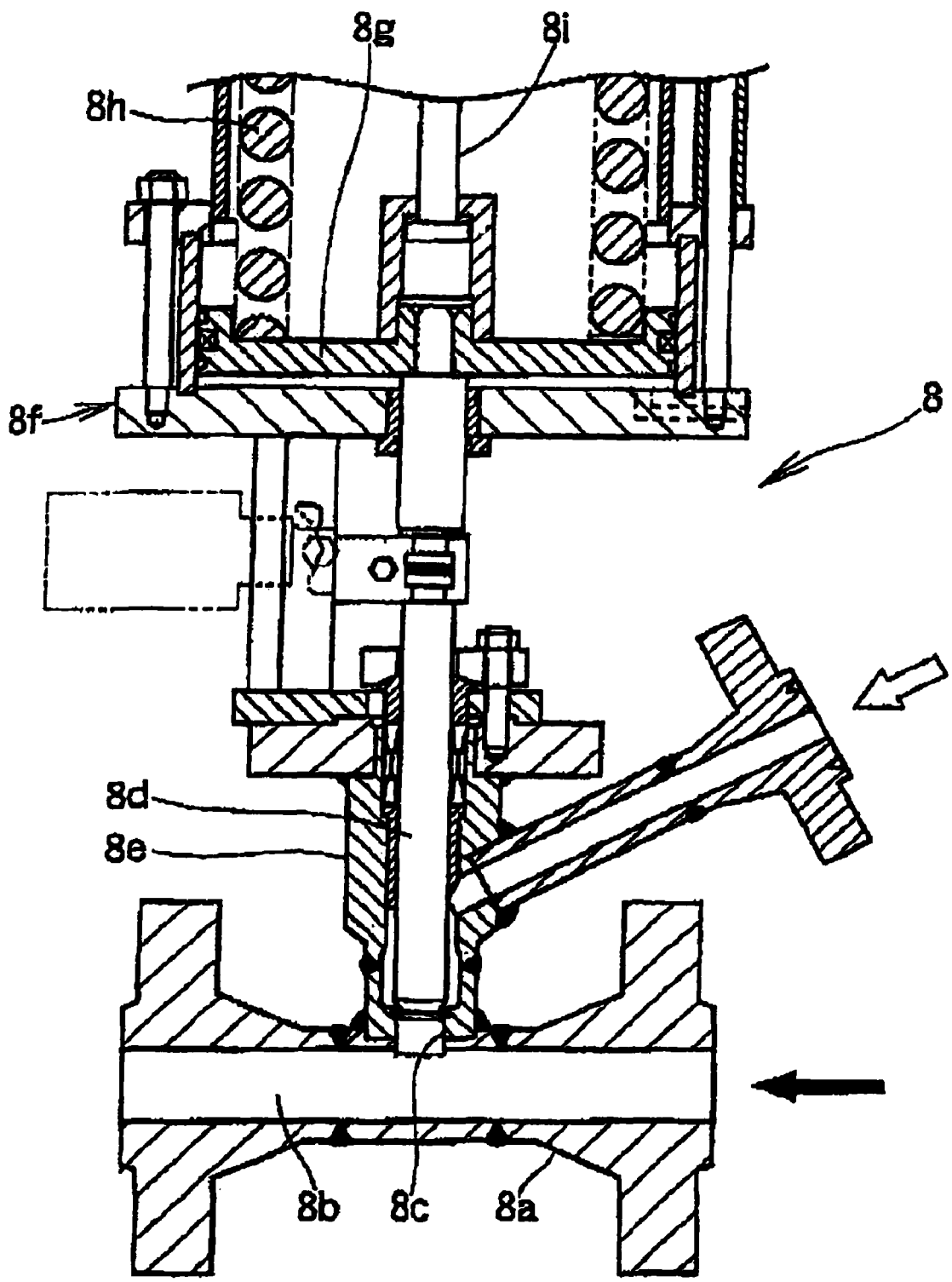
FIG. 3 is a cross sectional view for a main portion of an on-off valve of an apparatus for decomposing and recovering an isocyanate compound according to an embodiment of the invention.
Figure 4:
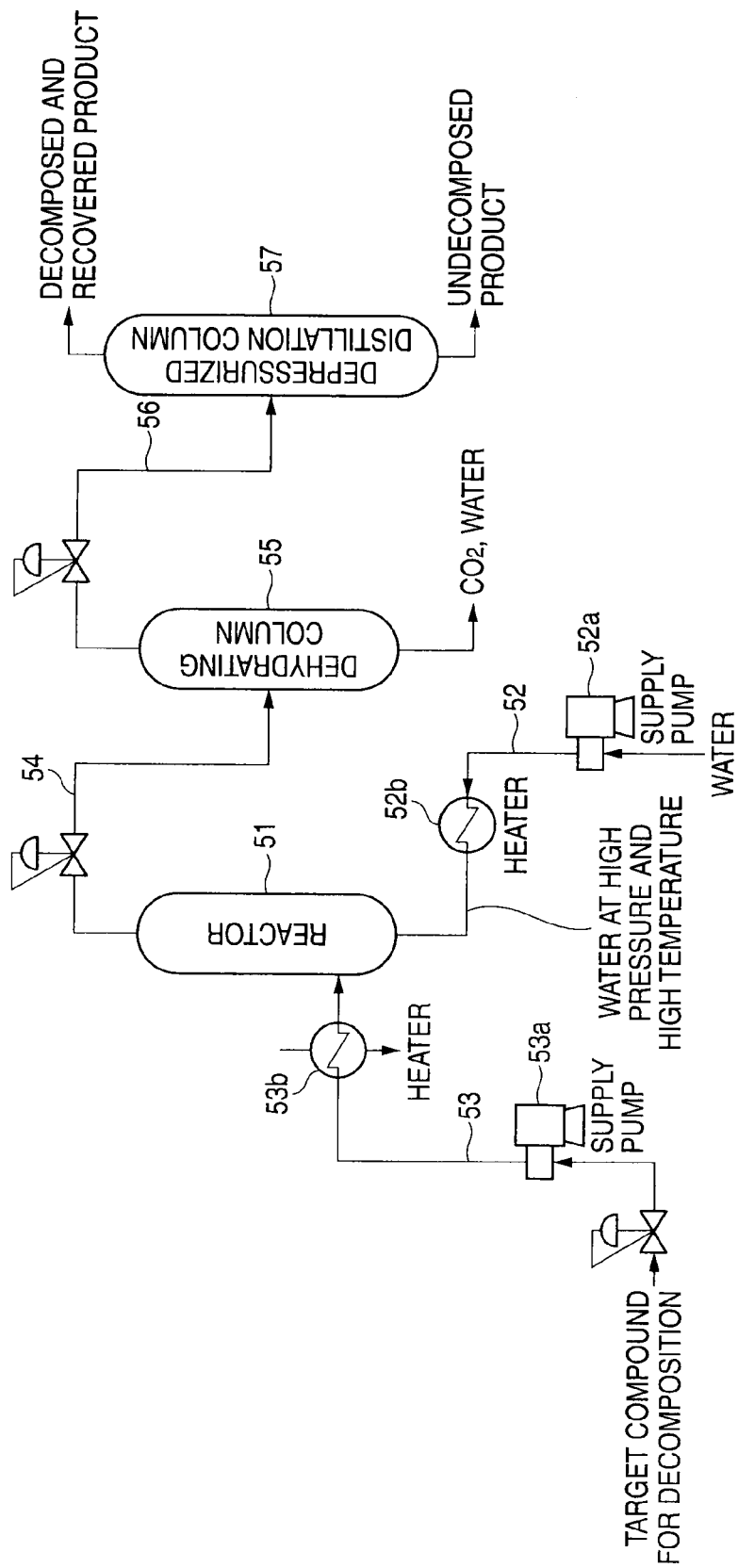
FIG. 4 is a schematic explanatory view showing an example of decomposing and recovering apparatus for practicing a method for decomposing and recovering the isocyanate compound according to the conventional example.

FIG. 1 is a schematic view showing an example of an apparatus for decomposing and recovering an isocyanate compound according to an embodiment of the invention, FIG. 2 is a cross sectional view of a reactor of the apparatus for decomposing and recovering an isocyanate compound according to an embodiment of the invention, and FIG. 3 is a cross sectional view for a main portion of an on-off valve of the apparatus for decomposing and recovering an isocyanate compound according to an embodiment of the invention.

Prior to the explanations of the constitution of the apparatus for decomposing and recovering an isocyanate compound according to an embodiment of the invention, the isocyanate compound as a target of decomposition is at first described. Examples of the isocyanate compound as the target of decomposition include all of compounds having at least one isocyanate group; compounds formed by dimerization reaction or trimerization reaction of these compounds having the isocyanate group into multimers such as dimers or trimers, for example, carbodiimide, urethidione, urethoneimine and isocyanurate; or compounds having a group (also including bond) derived from isocyanate group such as compounds having an urethane bond, alophanate bond, urea bond, buret bond, etc. formed from chemical reaction of isocyanate group-containing compounds with other functional group-containing compounds. This is similar to conventional examples described in JP-A-10-279539 and U.S. Pat. No. 6,630,517.

Since isocyanate groups or the groups derived from an isocyanate group in these compounds are hydrolyzed into an amino group (—$NH_2$) in the reactor 1, they can be recovered as amine compounds. Further, isocyanate compounds as typical examples of the isocyanate compounds as the object for hydrolysis used generally and amine compounds recovered from these compounds according to the invention are as shown in the following Table 1 and also such compounds are similar to those in the conventional examples described in JP-A-10-279539 and U.S. Pat. No. 6,630,517.

TABLE 1

| Isocyanate compound | Amine compound |
|---|---|
| phenyl isocyanate | aniline |
| tolylene diisocyanate (TDI) | tolylene diamine |
| diphenylmethane diisocyanate | diphenylmethane diamine |
| dianisidine diisocyanate | dianisidine diamine |
| tolydine diisocyanate | tolydine diamine |
| naphthalene diisocyanate | naphthalene diamine |
| hexamethylene diisocyanate | hexamethylene diamine |
| isophoron diisocyanate | isophoron diamine |
| meta-xylylene diisocyanate | meta-xylylene diamine |
| 2,2,4-trimethylhexamethylene diisocyanate | 2,2,4-trimethylhexamethylene diamine |
| dimeric acid diisocyanate | dimeric acid diamine |
| bisisocyanate methyl cyclohexane | bisamino methyl cyclohexane |
| isopropylidene biscyclohexane | isopropylidene biscyclohexyl diamine |
| methylcyclohexane diisocyanate | methylcyclohexane diamine |

Naturally, also compounds having a group or bond derived from isocyanate formed as a result of multimerizing chemical reaction or reaction with other functional group compounds of the diisocyanate compounds can also be recovered as corresponding amine compounds respectively. Such compounds as the target for decomposition are essentially contained substantially in wastes discharged as distillation residues in a purification and distillation step in chemical plants upon synthesis of isocyanate group-containing compounds. The invention intends to decompose the isocyanate compound obtained as the distillation residue by bringing it into contact with water at high pressure and high temperature thereby recovering it at a high efficiency as a raw material for the isocyanate compound or derivative thereof.

Successively, the water at high pressure and high temperature in the invention is described below. The temperature of the water at high pressure and high temperature is within a range of from 190 to 370° C., and preferably within a range of from 200 to 300° C. While the pressure of the water at high pressure and high temperature is not particularly restricted so long as it is within the range that the isocyanate compound may be decomposed in the range of the temperature described above, it is usually within a range of from 3 to 30 MPa.

The apparatus for decomposing and recovering an isocyanate compound for practicing the method for decomposing and recovering an isocyanate compound according to the invention has, for example, as shown in FIG. 1, a longitudinal cylindrical reactor 1 having a constitution to be described later, which is employed for conducting a decomposition reaction by bringing the water at high pressure and high temperature into contact with the isocyanate compound. A water supply line 2 having a supply pump 2a for pressurizing water supplied from a water supply source which is not illustrated and a heater 2b for heating high-pressure water pressurized with the supply pump 2a intervened therethrough is in communication with the bottom of the reactor 1. Further, a compound supply line 3 having a supply pump 3a for pressurizing the isocyanate compound in a molten state or solution state and a heater 3b for heating the isocyanate compound in a molten state or solution state pressurized with the supply pump 3a intervened therethrough is in communication with the vicinity of the communication portion of the water supply line 2 to the reactor 1, through an on-off valve 8 having the constitution to be described later.

In the apparatus for decomposing and recovering the isocyanate compound according to this embodiment, in order to rapidly disperse the isocyanate compound in the water at high pressure and high temperature, the supply pump 2a intervened in the water supply line 2 is operated such that the linear velocity of the water at high pressure and high temperature flowing through the communication portion of the compound supply line 3 for the water supply line 2 is at 0.5 m/s or higher. There is no particular restriction for the upper limit of the linear velocity of the water at high pressure and high temperature, it is preferably 3.0 m/s or less in view of the performance of the supply pump 2a, etc. On the other hand, the linear velocity of the isocyanate compound is desirably 0.3 m/s or higher, preferably 0.5 m/s or higher, and more preferably 1 m/s or higher. While the upper limit for the linear velocity of the isocyanate compound is not particularly restricted, it is preferably 8.0 m/s or less in view of the performance of the supply pump 3a, etc.

The linear velocity referred to in the present specification means a value obtained by dividing the flow rate by the cross section of the supply line. In the case where the flow rate fluctuates due to pulsation or the like, it means an average value thereof.

The supply pump 2a and the supply pump 3a each are preferably a multi-piston pump having a plurality of pistons. By the use of the multi-piston pump, pulsation upon supplying of the water at high pressure and high temperature and the isocyanate compound in a molten state or solution state to the reactor 1 can be decreased and a large amount of the isocyanate compound in a molten state or solution state and the water at high pressure and high temperature can be supplied in comparison with the case in which the pulsation is large. Accordingly, it is possible to obtain an excellent effect of contributing to the improvement for the recovery efficiency of the raw material for the isocyanate compound or the derivative thereof.

Further, a decomposition reaction product discharge line 4 for supplying the decomposition reaction product formed by decomposition with setting a temperature of the reactor 1 at 190 to 300° C. is in communication with the dehydrating column 5 as a dehydrating device from the decomposition reaction product discharge port at the top of the reactor 1. Further, a decomposition reaction product supply line 6 for supplying the decomposition reaction product which is dehydrated as well as removed with $CO_2$ in the dehydrating column 5 is in communication with a depressurized distillation column 7 as a purification device from the top of the dehydrating column 5. Then, it is constituted such that the decomposition reaction product which is dehydrated as well as removed with $CO_2$ by distillation in the depressurized distillation column 7 is separated into the aimed decomposed and recovered product (raw material for the isocyanate compound or the derivative thereof) and undecomposed product (undecomposed compound).

The reactor 1 is constituted, for example, as shown in FIG. 2. That is, the reactor 1 includes: a vertical cylindrical vessel body 11 having a discharge port 11a for the decomposition reaction product at the top thereof and a liquid mixture supply port 11b in communication with the water supply line at the bottom thereof, and a liquid swirling device 12 contained in the vessel body 11 for ascending a liquid mixture entering from the liquid mixture supply port 11b as a swirling flow. The liquid swirling device 12 includes: a rod-like blade support member 12a disposed at the radial center of the vessel body 11; and spiral blades 12b fixed spirally to the blade support member 12a, the spiral blades each having an outer peripheral end which contacts with the inner peripheral face of the vessel body 11.

The on-off valve is constituted, for example, as shown in FIG. 3. That is, the on-off valve 8 includes a water flow tubular member 8a intervened in the water supply line 2, the water flow tubular member having a water flow channel 8b through which the water at high pressure and high temperature flows. Into the water flow channel 8b of the water flow tubular member 8a, a compound supply port 8c through which the isocyanate compound in a molten state or solution state supplied from the compound supply line 3 flows out is opened, and there is provided a retractable valve rod 8d that protrudes somewhat at the top end thereof from the compound supply port 8c into the water flow channel 8b to inhibit the inflow of the water at high pressure and high temperature to the compound supply port 8c in a closed state where the outflow of the isocyanate compound into the water flow channel 8b is shut off.

The valve rod 8d penetrates through the on-off valve 8 having the compound supply port 8c, and it is constituted so as to move backward to the position for the open state by the supply of a pressurized air to an air cylinder 8f disposed on the base end of the valve rod 8d and to move forward to a position for the closed state by a coil spring 8h that presses the piston 8g of the air cylinder 8f. A valve rod stroke control rod 8i having at the top end thereof a stopper for suppressing the ascending amount of the piston 8g is connected through a connecting fitting at the center in the upper portion of the piston 8g, and it is constituted so as to move forward and backward (upward and downward) by normal and reverse rotation of a handle which is not illustrated. Further, a compound introduction port which is introduced with the isocyanate compound and is in communication with the compound supply port 8c is protruded obliquely on the lateral side of the valve box 8e.

In the case of the on-off valve 8 of the embodiment described above, as can be best understood by the above descriptions, the isocyanate compound in a molten state or solution state flows from the compound introduction port into the on-off valve 8, and it is constituted such that the compound supply port 8c is closed by the valve rod 8d that moves forward and backward in the isocyanate compound in a molten state or solution state. However, the on-off valve 8 of the invention is not particularly restricted to the constitution described above.

It may be constituted, for example, such that the compound supply line 3 is in communication in a perpendicular state with the water supply line 2, an on-off valve is disposed on the counter-communication side of the compound supply line 3 while putting the water supply line 2 therebetween and the retractable valve rod of the on-off valve traversely penetrates from one to the other side of the flow channel of the water supply line 2.

Then, it may also be constituted such that the top end of the valve rod of the on-off valve intrudes into the opening in the water supply line 2 of the compound supply line 3 to thereby shut off the opening.

The operation mode of the apparatus for decomposing and recovering the isocyanate compound according to an embodiment of the invention is described below. That is, according to the apparatus for decomposing and recovering the isocyanate compound, the isocyanate compound in a molten state or solution state is supplied continuously into the water flow channel 8b of the water flow tubular member 8a intervened in the water supply line 2 and mixed into a water at high pressure and high temperature flowing at a linear velocity of 0.5 m/s or higher. Accordingly, the isocyanate compound in a molten state or solution state is rapidly dispersed in the water at high pressure and high temperature without the necessity of elongating the reactor 1. Then, since the isocyanate compound in the liquid mixture containing the isocyanate compound and the water at high pressure and high temperature supplied continuously to the reactor 1 is put to decomposition reaction at a high efficiency in the reactor 1, the recovery efficiency of the raw material for the isocyanate compound or the derivative thereof may be improved.

Further, according to the apparatus for decomposing and recovering the isocyanate compound of an embodiment according to the invention, the liquid mixture containing the isocyanate compound and the water at high pressure and high temperature flowing into the reactor 1 ascends as a swirling flow along the spiral blades 12b of the liquid swirling device 12. Accordingly, since $CO_2$ generated by the decomposition reaction of the isocyanate compound ascends as bubbles accompanying the swirling flow, $CO_2$ does not blow out above the reactor 1. Therefore, the decomposition reaction product can be supplied from the reactor 1 to the dehydrating column 5 without any trouble and can contribute to the improvement of the recovery efficiency of the raw material for the isocyanate compound or the derivative thereof.

Further, in the apparatus for decomposing and recovering the isocyanate compound according to an embodiment of the invention, the on-off valve 8 has a retractable valve rod 8d that protrudes from the compound supply port 8c into the water flow channel 8b to thereby inhibit the inflow of the water at high pressure and high temperature into the compound supply port 8c in a closed state where the outflow of the isocyanate compound into the water flow channel 8b is shut out. Therefore, the water at high pressure and high temperature does not stay at the compound supply port 8c in the closed state and the isocyanate compound intrudes into the water at high pressure and high temperature flowing at a high linear velocity at the same time with the opening of the valve.

Consequently, according to the apparatus for decomposing and recovering the isocyanate compound of an embodiment according to the invention, since the isocyanate compound does not cause polymerization due to the staying of the water at high pressure and high temperature at the compound supply pump 8c and the compound supply pump 8c is not clogged, the isocyanate compound can be mixed into the water at high pressure and high temperature without any trouble. Therefore, it is possible to obtain an excellent effect of contributing to the continuation of the stable operation of the apparatus for decomposing and recovering the isocyanate compound and to the improvement in the recovery efficiency of the raw material for the isocyanate compound or the derivative thereof.

As has been described above, according to the method for decomposing and recovering the isocyanate compound and the apparatus for decomposing and recovering the same according to the invention, the isocyanate group or the group derived from the isocyanate group of the isocyanate compound can be decomposed at a high efficiency, and the raw material for the isocyanate compound or the derivative thereof can be recovered at a high recovery efficiency. Accordingly, they can greatly contribute also to the regenerative use of distillation residues, resource preservation, and environmental protection. Isocyanate compounds as the target of the decomposition in the invention is not restricted to those in the distillation residues of chemical plants so long as they are isocyanate compounds having at least one isocyanate group or group derived from an isocyanate group.

In "Best Mode for Carrying out the Invention" in the present specification, detailed descriptions regarding the operation conditions for "apparatus for decomposing and recovering the isocyanate compound" are omitted but it may be practiced under the same conditions as those in conventional examples described in JP-A-10-279539 and U.S. Pat. No. 6,630,517, the entire content thereof being hereby incorporated by reference. Various conditions on the operation of the apparatus for decomposing and recovering the isocyanate compound include melting temperature and the introduction temperature of the isocyanate compound, solvent for the isocyanate compound, the ratio for supplying the isocyanate compound in a molten state or solution state and the water at high pressure and high temperature to the reactor, the decomposition reaction temperature and the reaction pressure of the isocyanate compound in the reactor, the dehydrating temperature for the decomposition reaction product in the dehydrating column, the distillation temperature for the decomposition reaction product after dehydrating in the depressurized distillation column.

The present invention will be described more specifically with reference to an example, but the invention is not restricted at all to such example. Material, amount of use, ratio, contents of processing, processing procedures shown in the following example can be changed properly so long as they do not depart from the gist of the invention.

EXAMPLE

An experiment was conducted by using distillation residues discarded from a chemical plant for synthesizing tolylene diisocyanate (TDI) and decomposing and recovering them as tolylene diamine (TDA), i.e., an intermediate material for TDI. The distillation residues were composed of about 10% by weight of TDI and about 90% by weight of dimer or higher multimer of TDI. The distillation residues were used as the target compound for decomposition, and the distillation residues were decomposed by using the decomposition reaction apparatus shown in FIG. 1 at a temperature in the reactor of 250° C. and at a pressure therein of 15 MPa. The distillation residues were heated with the heater (3b) to 150° C. and continuously supplied at a flow rate of 0.5 L/s. In this case, the linear velocity in the supply line (3) was 1 m/s. Water was heated with the heater (2b) to 250° C. and supplied continuously at a flow rate of 1 L/s. The operation was conducted continuously for 1000 hours while controlling the staying time of the distillation residues in the reactor to 0.4 hours and the apparatus could be operated stably without causing any problem such as clogging. The average yield of TDA was 90% (yield from 2 hours after reaching a stationary state after starting the operation to the end).

The constitution for the apparatus for decomposing and recovering the isocyanate compound according to the invention described above is merely one specific example of the invention and the invention is not restricted to the constitution of the embodiment described above. Further, the design concerning the constitution of the apparatus for decomposing and recovering the isocyanate compound according to the invention can be optionally modified so long as it is within a range not departing from the technical idea of the invention.

While the present invention has been described in detail and with reference to specific embodiments thereof, it will be apparent to one skilled in the art that various changes and modifications can be made therein without departing from the scope thereof.

This application is based on Japanese patent application No. 2005-202419 filed Jul. 12, 2007, the entire contents thereof being hereby incorporated by reference.

Further, all references cited herein are incorporated in their entireties.

INDUSTRIAL APPLICABILITY

According to the apparatus for decomposing and recovering the isocyanate compound of the invention, since the isocyanate compound in a molten state or solution state is continuously mixed into the water at high pressure and high temperature at high linear velocity, the isocyanate compound can be dispersed rapidly in the water at high pressure and high temperature without any requirement for elongating the reactor. Then, since the isocyanate compound in the liquid mixture containing the isocyanate compound and the water at high pressure and high temperature supplied continuously to the reactor is subjected to decomposition reaction at a high efficiency in the reactor, the recovery efficiency of the raw material for the isocyanate compound or the derivative thereof is increased.

The invention claimed is:

1. An apparatus for decomposing and recovering an isocyanate compound, which comprises:
   a reactor adapted to bring water at high pressure and high temperature into contact with an isocyanate compound having at least one isocyanate group or group derived from an isocyanate group to cause a decomposition reaction;
   a water supply line adapted to continuously supply the water at high pressure and high temperature to the reactor;
   a compound supply line adapted to continuously supply isocyanate compound in a molten state or solution state to the water supply line;
   an on-off valve adapted to communicate the compound supply line with a vicinity of a communication portion of the water supply line to the reactor;
   a dehydrating device adapted to conduct a dehydration of a decomposition reaction product discharged from the reactor; and
   a purification device adapted to purify the decomposition reaction product after the dehydration, wherein
   the reactor includes:
   a vertical cylindrical vessel body having a discharge port for the decomposition reaction product at the top thereof and a liquid mixture supply port in communication with the water supply line at the bottom thereof, and
   a liquid swirling device disposed in the vessel body, which ascends a liquid mixture entering from the liquid mixture supply port as a swirling flow, and
   wherein the liquid swirling device includes:
   a blade support member disposed at the radial center of the vessel body, and
   a spiral blade fixed spirally to the blade support member, the spiral blade having an outer circumferential end which contacts with the inner peripheral surface of the vessel body.

2. The apparatus for decomposing and recovering an isocyanate compound according to claim 1, wherein the on-off valve includes:
   a water flow tubular member intervened in the water supply line, the water flow tubular member having a water flow channel through which the water at high pressure and high temperature flows,
   a compound supply port opened into the water flow channel, which is adapted so that the isocyanate compound in a molten state or solution state supplied from the compound supply line flows out from the compound supply port, and
   a retractable valve rod adapted to inhibit an inflow of the water at high pressure and high temperature into the compound supply port in a closed state in which an outflow of the isocyanate compound into the water flow channel is shut off.

3. The apparatus for decomposing and recovering an isocyanate compound as a decomposition target according to claim 1, wherein the water at high pressure and high temperature and the isocyanate compound in a molten state or solution state are respectively supplied under pressure with a multi piston pump.

4. The apparatus for decomposing and recovering an isocyanate compound as a decomposition target according to claim 2, wherein the water at high pressure and high temperature and the isocyanate compound in a molten state or solution state are respectively supplied under pressure with a multi piston pump.

* * * * *